United States Patent [19]

Bochis et al.

[11] Patent Number: 4,816,469

[45] Date of Patent: Mar. 28, 1989

[54] 5-AMINO OR SUBSTITUTED AMINO 1,2,3-TRIAZOLES

[75] Inventors: Richard J. Bochis, East Brunswick; Richard L. Tolman, Warren; Elbert Harris, Westfield, all of N.J.

[73] Assignee: Merck & Co., Inc., Rahway, N.J.

[21] Appl. No.: 117,773

[22] Filed: Nov. 6, 1987

Related U.S. Application Data

[60] Division of Ser. No. 864,651, May 19, 1986, Pat. No. 4,721,791, which is a continuation-in-part of Ser. No. 576,302, Feb. 2, 1984, abandoned.

[51] Int. Cl.[4] ............................................ C07D 249/06
[52] U.S. Cl. .................................... 514/359; 548/255; 546/175; 546/256
[58] Field of Search ......................... 548/255; 574/359

[56] References Cited

U.S. PATENT DOCUMENTS 4,590,201  5/1986  Bochis et al. ........................ 514/359

OTHER PUBLICATIONS

Ferlauts, R. "Controlling Coccidiosis in Poultry Employing Triazole Derivatives" GA 75 87461w (1971).
Albert, A. "V-Triazolo [4,5-d] pyrimidines (8 azapurine), Part 24" GA 95 150600u (1981).
Colautti et al. "New Coccidiostatic Drugs of the 4-Amine-4H-1,2,4 Triazole Series" CA 76 99512s (1972).
Hamada et al, "Triazole Anticoccidium Agents" CA 83 126969e (1975).

Primary Examiner—Glennon H. Hollrah
Assistant Examiner—A. A. Owens
Attorney, Agent, or Firm—David L. Rose; Michael C. Sudol

[57] ABSTRACT

Novel 5-amino or substituted amino 1,2,3-triazoles are disclosed as having anticoccidial activity. The compounds are useful for controlling coccidiosis when administered in minor quantities to animals, in particular to poultry, usually in admixture with animal sustenance.

6 Claims, No Drawings

5-AMINO OR SUBSTITUTED AMINO 1,2,3-TRIAZOLES

CROSS REFERENCE TO RELATED APPLICATIONS

This is a division of application Ser. No. 864,651, filed May 19, 1986, now U.S. Pat. No. 4,721,791 which is a continuation-in-part of U.S. Pat. No. 576,302 filed Feb. 2, 1984, now abandoned.

BACKGROUND OF THE INVENTION

This invention relates to new chemical compounds and the method of the preparation of the same. It relates further to the use of such new compounds for treating and preventing coccidiosis. This invention still more particularly relates to novel 5-amino and substituted amino 1,2,3-triazole compounds and substituted derivatives thereof and the use of the same in the control and treatment of coccidiosis Coccidiosis is a wide-spread poultry disease which is produced by infections of protozoa of the genus Eimeria which causes severe pathology in the intestines and ceca of poultry. Some of the most significant of these species are E. tenella, E. acervulina, E. Necatrix, E. brunetti, E. maxima, E. mitis, E. mivati, E. hagani and E. praecox. This disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection. Coccidiosis is therefore a disease of great economic importance and extensive work has been done to find new and improved methods for controlling and treating coccidial infections in poultry.

SUMMARY OF THE INVENTION

This invention is based on the discovery that certain novel 5-amino and substituted amino 1,2,3-triazoles as well as substituted derivatives thereof have a surprisingly and unexpectedly high degree of activity against coccidiosis of poultry. Administration of a small amount of at least one of these compounds preferably by combination with poultry feed is effective in preventing or greatly reducing the incidence of coccidiosis. The compounds are effective against both the cecal form (caused principally by E. tenella) and the intestinal forms (principally caused by E. acervulina, E. brunetti. E. maxima and E. necatrix). The coccidiostats of this invention are particularly effective against the species that cause cecal damage in addition to preventing the pathology caused by the coccidia.

The instant compounds are also active against Eimeria spp, in other animals.

The 1,2,3-triazole derivatives may be prepared by reacting appropriately substituted nitriles with appropriately substituted azides in the presence of a base in a suitable reaction medium to obtain such novel 5-amino-1-substituted-1,2,3-triazoles.

Some of the novel 1,2,3-triazole derivatives of this invention may also be prepared by reacting an appropriately substituted halide and a 1-unsubstituted 1,2,3-triazole compound in the presence of a base in a suitable reaction medium to obtain such novel 5-amino or substituted amino 1-substituted 1,2,3-triazoles The novel 1,2,3-triazole derivatives of this invention may also be prepared by reaction of a 1-substituted 5-amino-1,2,3-triazole compound with an appropriately substituted halide in the presence of a base in a suitable reaction medium to obtain such novel 1-substituted-5-substituted amino 1,2,3-triazoles.

It is therefore a primary object of this invention to provide novel 5-amino or substituted amino 1,2,3-triazoles with appropriate substitutions at the 1, 4 and 5-positions which are useful in the control of coccidiosis. Still another object of this invention is to provide novel feed compositions useful for the prevention and suppression of coccidiosis. A further object of this invention is to provide a new and useful method for the control of coccidiosis in poultry which comprises administering to the poultry minor amounts of the anticoccidial substance of this invention. A still further object of this invention is to provide a method and alternate methods for preparing novel 5-amino and substituted amino 1,2,3-triazoles. These and further objects of this invention will become apparent from reading the following description.

DESCRIPTION OF THE INVENTION

The novel compounds of this invention are best realized in the following structural formula:

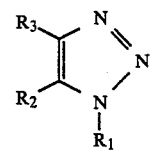

wherein:

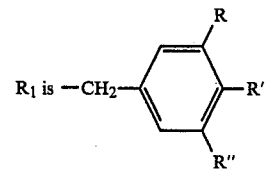

wherein one of R, R' and R" is trichlorovinyl and the other two of R, R' and R" are selected from hydrogen, halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl The preferred novel compounds of the instant invention are realized in the above structural formula when one of R, R' and R" is trichlorovinyl and the other two of R, R' and R" are selected from hydrogen, halogen, cyano, trifluoromethyl, trichlorovinyl or methyl;

$R_2$ is amino; and $R_3$ is carbamoyl.

Further preferred compounds of this invention are realized where R is trichlorovinyl, R' is hydrogen and R" is selected from halogen, cyano, trifluoromethyl or methyl.

The most preferred compounds of this invention are realized when R is trichlorovinyl and R' is hydrogen and R" is halogen or trifluoromethyl.

Examples of the preferred novel compounds of this invention are:

5-amino-1-[3-chloro-5-(trichlorovinyl)benzyl]1,2,3-triazole-4-carboxamide;
5-amino-1-(4-trichlorovinylbenzyl)-1,2,3-triazole-4-carboxamide;
5-amino-1-[3-bromo-5-(trichlorovinyl)benzyl]-1,2,3-triazole-4-carboxamide;
5-amino-1-[3-fluoro-5-(trichlorovinyl)benzyl]-1,2,3-triazole-4-carboxamide;
5-amino-1-[3-trifluoromethyl-5-(trichlorovinyl)benzyl]-1,2,3-triazole-4-carboxamide;
5-amino-1-[3,5-di(trichlorovinyl)benzyl]1,2,3-triazole-4-carboxamide;
5-amino-1-[3-chloro-4-(trichlorovinyl)benzyl]-1,2,3-triazole-4-carboxamide;
5-amino-1-[4-chloro-3-(trichlorovinyl)benzyl]-1,2,3-triazole-4-carboxamide;
5-amino-1-[3,5-dichloro-4-(trichlorovinyl)benzyl]-1,2,3-triazole-4-carboxamide.

A further aspect of this invention involves the use of the above novel compounds, and other structurally related compounds in novel compositions and methods for the treatment of coccidiosis. The novel compositions and methods of this invention, which include the above novel compounds, are best realized in the following structural formula:

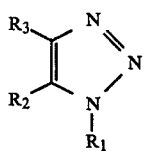

wherein:
R$_1$ is phenyl, phenyl loweralkyl, substituted phenyl or substituted phenyl loweralkyl wherein the substituents are 1 to 5 of halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

R$_1$ may also be phenacyl, pyridyl, pyridylmethyl, naphthyl, naphthylmethyl, quinolyl or quinolylmethyl; and R$_2$ and R$_3$ are as defined above.

The preferred compounds forming the active ingredient in the novel compositions and methods of the instant invention are realized in the foregoing structural formula wherein:
R$_1$ is mono- di- or tri-substituted phenyl or mono- di- or tri-substituted benzyl wherein the substituents are halogen, cyano, trifluoromethyl, trichlorovinyl or methyl;
R$_2$ is amino; and
R$_3$ is carbamoyl.

The most preferred compounds of the instant novel compositions and methods of the instant invention are realized in the foregoing structural formula wherein R$_1$ is di- or tri-substituted phenyl or di- or tri-substituted benzyl, and wherein the substituents are in the meta or para positions and are chloro, cyano, methyl, trifluoromethyl, or trichlorovinyl;
R$_2$ is amino; and
R$_3$ is carbamoyl.

Examples of preferred compounds of the novel compositions and methods of this invention are, in addition to the specific compounds named above:

5-amino-1-(3,4-dichlorobenzyl)-1,2,3-triazole-4-carboxamide,
5-amino-1-(3,4,5-trichlorobenzyl)-1,2,3-triazole-4-carboxamide,
5-amino-1-(4-chloro-3-trifluoromethylbenzyl)-1,2,3-triazole-4-carboxamide, In the instant invention the term "loweralkyl" is intended to include those alkyl groups containing from 1 to 3 carbon atoms. Exemplary of such groups are methyl, ethyl, propyl and isopropyl.

The term "loweralkoxy" is intended to include those alkoxy groups containing from 1 to 3 carbon atoms. Exemplary of such groups are methoxy, ethoxy, propoxy, and isopropoxy.

The term "loweralkanoyl" is intended to include those alkanoyl groups containing 1 to 3 carbon atoms exemplified by formyl, acetyl, and propionyl.

The compounds of the instant invention may be prepared by any one of several processes. The most general process is outlined in the following reaction scheme.

Reaction Scheme I

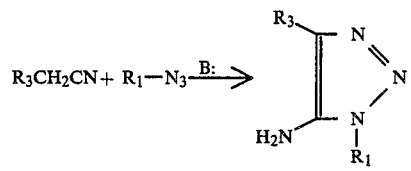

wherein an R$_3$-methylene substituted nitrile is allowed to react with an R$_1$ substituted azide in the presence of a base to provide the desired 5-amino- 1-substituted-1,2,3-triazole. The reaction is carried out in solvents such as aromatic hydrocarbons, lower alkanols, dimethylformamide, dimethylsulfoxide or hexamethylphosphoric triamide. The base may be any alkali metal or alkaline earth hydroxide, alkoxide or hydride such as sodium ethoxide, potassium t-butoxide, magnesium ethoxide, sodium hydroxide or sodium hydride, chosen to be compatible with the reaction solvent. Generally the reaction is conducted at from −40° C. to 100° C. and is complete in from 15 minutes to 48 hours. The product of the reaction is isolated by techniques known to those skilled in the art.

Reaction Scheme II

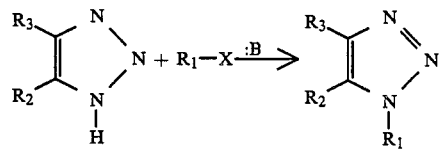

wherein X is a halogen, preferably chlorine or bromine. In the foregoing reaction a 1-unsubstituted but otherwise appropriately substituted 1,2,3-triazole is reacted with a halogen substituted R$_1$ group in the presence of a base to prepare the desired 1-substituted 1,2,3-triazole. The reaction is carried out in a solvent which may be any polar aprotic organic solvent such as dimethylformamide, dimethylsulfoxide, acetonitrile, dioxane, and the like in the presence of a base. The base may be any non-nucleophilic organic or inorganic base. Suitable inorganic bases are alkali metal bases, such as sodium and potassium carbonates, phosphates, bicarbonates and hydroxides, or sodium hydride, chosen for compatibility with the reaction solvent. Suitable organic bases are tertiary amines such as trialkyl substituted amines. The reaction rate varies greatly with the nature of the proposed substituent at the $R_1$ position, the base being used in the reaction and the solvent. Very reactive substituent and base combinations may be complete in as little as ten minutes and at the other extreme the reaction may take as long as two weeks. Most reactions are however complete in from 1 to 100 hours. The reaction is carried out at a temperature of from room temperature to 100° C. or to the reflux temperature of the solvent system being used. The products of the reaction are isolated using techniques known to those skilled in the art.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not cause any undesirable effects.

A feed typically contains from about 0.001 to about 0.2 percent, preferably from about 0.003 to about 0.1 percent, by weight of one of the coccidiostats of this invention. The optimum levels will naturally vary with the specific compound utilized and species of Eimeria involved, and can be readily determined by one skilled in the art. Levels of the 5-amino and substituted amino 1,2,3-triazoles of this invention, in poultry feed of from about 0.003 percent to about 0.1 percent by weight of the diet are especially useful in controlling the pathology associated with E. tenella, as well as the intestinal dwelling species.

Depending on the compound employed, levels as low as 0.001 percent possess the novel effects of reducing the number of oocysts passed in the droppings of infected chickens.

The quantity or concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The following non-limiting examples will serve to further illustrate the instant invention.

EXAMPLE 1

5-Amino-1-(3,4-dichlorobenzyl)-1,2,3-triazole-4-carboxamide

Method A

A stirred mixture of 3,4-dichlorobenzyl chloride (12.6 g, 64.5 mmol) and sodium azide (7.0 g, 0.11 mole) in absolute ethanol (70 ml) was refluxed for 4.75 hours, cooled and filtered to provide a solution of 3,4-dichlorobenzyl azide. Separately, 2-cyanoacetamide (5.5 g, 65 mmol) was added to a 35° C. solution of sodium (1.5 g, 65 mmol) in absolute ethanol (125 ml), and to the resulting suspension was added the above azide solution dropwise over 10 minutes. The combined mixtures were refluxed for 1 hour, kept 16 hours at ambient temperature and 1 hour at 5° C., and filtered. The crude product was dried under vacuum, dissolved in boiling ethanol (290 ml), filtered hot, and cooled to 0° C. The solid was collected by filtration and dried under vacuum to provide 12.4 g (67%) of 1-(3,4-dichlorobenzyl)-5-amino-1,2,3-triazole-4-carboxamide, m.p. 221°–222° C.

Method B

A stirred, ambient temperature solution of 5-amino-1,2,3-triazole-4-carboxamide (635 mg, 5.00 mmole) in dry dimethylformamide (20ml) is treated in one portion with sodium hydride (240 mg of a 5% dispersion in mineral oil, 120 mg NaH, 5.0 mmol). After 15 min 3,4-dichlorobenzyl chloride (0.977 g, 5.00 mmol) is added. The mixture is stirred 1 hour, poured into water (20 ml), acidified to pH 6 with glacial acetic acid, and filtered. The solid is washed with water, dried, and chromatographed to provide 5-amino-1-(3,4-dichlorobenzyl)-1,2,3-triazole-4-carboxamide.

EXAMPLE 2

5-Amino-1-(4-methylbenzyl)-1,2,3-triazole-4-carboxamide

A stirred mixture of 4-methylbenzyl bromide (1.3 g, 7.0 mmol) and sodium azide (754 mg, 11.6 mmol) in ethanol (8 ml) was refluxed under a nitrogen atmosphere for 3 hours, cooled to ambient temperature, and filtered. Separately, 2-cyanoacetamide (588 mg, 7.0 mmol) was added to a stirred, refluxing solution of sodium (167 mg, 7 2 mmol) in ethanol (15 ml), followed by dropwise addition of the above azide solution over 20 min. The resulting slurry was refluxed 1 hour, cooled to ambient temperature, and refrigerated. The precipitate was collected by filtration, washed with ethanol, and dried under vacuum to provide 1.12 g (69%) of 1-(4-methylbenzyl)5-amino-1,2,3-triazole-4-carboxamide, m.p. 223°–225° C.

EXAMPLE 3

4-Chloro-3-cyanobenzyl bromide

A mixture of 2-chloro-5-methylbenzonitrile (10.6 g, 69.9 mmol), N-bromosuccinimide (12.2 g, 68.5 mmol), and dibenzoyl peroxide (349 mg, 1.44 mmol) in benzene (350 ml) was refluxed 1.5 hours, cooled, and evaporated to dryness under vacuum. The residue was suspended in 7:3 (v/v) hexane-dichloromethane, filtered, and evaporated. The crude product was chromatographed on silica gel (650 g) eluted with 7:3 (v/v) hexane-dichloromethane to provide 4.8 g (30%) 4-chloro-3-cyanobenzyl bromide, m.p. 55°–58° C.

EXAMPLE 4

4-Chloro-3-cyanobenzyl azide

A stirred mixture of 4-chloro-3-cyanobenzyl bromide (3.0 g, 13 mmol) and sodium azide (1.26 g, 19.4 mmol) was refluxed 5 hours in absolute ethanol (30 mL). The mixture was kept 18 hours at ambient temperature, filtered, and the filtrate was evaporated under vacuum. The residue was triturated with diethyl ether, filtered, and evaporated to provide 2.45 g (98%) liquid 4-chloro-3-cyanobenzyl azide; I.R. (neat): 2240, 2100 cm$^1$.

EXAMPLE 5

5-Amino-1-(4-chloro-3-cyanobenzyl)-1,2,3-triazole-4-carboxamide

A stirred suspension of 2-cyanoacetamide (790 mg, 9.40 mmol) in absolute ethanol (40 ml) was treated with sodium methoxide (495 mg, 9.16 mmol) and refluxed 10 minutes. The mixture was cooled slightly, a solution of 4-chloro-3-cyanobenzyl azide (1.35 g, 7.01 mmol) in absolute ethanol (10 ml) was added in one portion, and the mixture was refluxed 2.5 hours. The mixture was filtered hot, the solid was washed with absolute ethanol, and the combined filtrate and wash were evaporated to dryness under vacuum. The residue was triturated with diethyl ether, filtered, and washed twice with diethyl ether. The solid was recrystallized from methanol (6 ml) and dried at 65° C. under vacuum to provide 635 mg (24%) 5-amino-1-(4-chloro-3-cyanobenzyl)-1,2,3-triazole-4-carboxamide, m.p. 172°–175° C.

EXAMPLE 6

1-(3,4-Dichlorobenzyl)-5-methylamino-1,2,3-triazole-4-carboxamide

A mixture of 5-amino-1-(3,4-dichlorobenzyl)-1,2,3-triazole-4-carboxamide (2.86 g, 10.0 mmol), methyl iodide (1.42 g, 10.0 mmol), and potassium carbonate (1.38 g, 10 0 mmol) in N,N-dimethylformamide (20 ml) is stirred 48 hours at ambient temperature, poured into water (150 ml), and filtered. Chromatography provides 1-(3,4-dichloro- benzyl)-5-methylamino-1,2,3-triazole-4-carboxamide.

EXAMPLE 7

5-Amino-1-(4-chloro-3-cyanobenzyl)-1,2,3-triazole-4-carboxamide

A stirred suspension of 2-cyanoacetamide (790 mg, 9.4 mmol) in absolute ethanol (40 ml) was treated with sodium methoxide (495 mg, 9.2 mmol) and refluxed 10 minutes. The mixture was cooled lightly, a solution of 4-chloro-3-cyanobenzyl azide (1.35 g, 7.0 mmol) in absolute ethanol was added, an the mixture was refluxed 2.5 hours. The mixture was filtered hot and the filtrate evaporated under vacuum. The residue was triturated with diethyl ether, filtered, and washed twice with diethyl ether. The solid was crystallized from refluxing methanol, filtered, washed twice with methanol and once with diethyl ether, and dried at 65° C. under vacuum to provide 635 mg (33%) 5-amino-1-(4-chloro-3-cyanobenzyl)-1,2,3-triazole-4-carboxamide, m.p. 172°–175° C.

EXAMPLE 8

5-Amino-1-(4-cyano-3,5-dichlorobenzyl)-1,2,3-triazole-4-carboxamide

A stirred, ambient temperature solution of 5-amino-1,2,3-triazole-4-carboxamide (630 mg, 5.0 mmol) in dry N,N-dimethylformamide (20 ml) was treated with sodium hydride (250 mg of a 50% dispersion in mineral oil, 125 mg NaH, 5.2 mmol). The resulting suspension was stirred 10 min., 4-cyano-3,5-dichlorobenzyl chloride (1.1 g, 5.0 mmol) was added, and the mixture was stirred 2 hours. The reaction was quenched by pouring into ice and water (80 ml). The suspension was filtered and washed three times with water. The solid was suspended in 19:1 (v/v) dichloromethane-methanol and filtered to provide 364 mg (23%) 5-amino-1-(4-cyano-3,5-dichlorobenzyl)-1,2,3-triazole-4-carboxamide. Recrystallization from ethanol provided material of m.p 238°–239.5° C.

EXAMPLE 9

3-Chloro-5-methylbenzyl bromide

A solution of 5-chloro-m-xylene (59.3 g) and dibenzoyl peroxide (5.0 g) in 1.13 L of benzene was heated at reflux. N-Bromosuccinimide (82.2 g) was added in portions over 15 minutes. Heating was continued for an additional 20 minutes until a negative potassium iodide reaction was observed. The reaction mixture was cooled, evaporated and then titurated with hexane (500 ml). The precipitated succinimide was removed by filtration and washed with additional hexane. Concentration afforded 101 g of crude 3-chloro-5-methylbenzyl bromide.

EXAMPLE 10

3-Chloro-5-methylbenzyl alcohol

A solution of crude 3-chloro-5-methylbenzyl bromide (49.68 g) in 300 ml of glacial acetic acid containing 48.54 g of KOAc was heated at reflux for 3 hours. The mixture was concentrated and then partitioned between water (600 ml) and ether (500 ml). After repeated extractions with ether, the combined organic layers were washed with saturated NaHCO$_3$ solution (300 ml) and water (300 ml). After treatment with MgSO$_4$, the ethereal solution was concentrated to give an oil, 41.5 g.

The crude acetate was dissolved in 200 ml of methanol and treated slowly with a methanolic KOH solution (33.4 g in 100 ml). The reaction mixture was stirred for 35 minutes at room temperature. The reaction mixture was neutralized with acetic acid and concentrated under reduced pressure. The residue was partitioned between water (300 ml) and ether (200 ml). Concentration afforded 27.9 g of crude product which was purified by silica gel chromatography (Eluant 95:5 CH$_2$Cl$_2$/Et$_2$O) to give 15.6 g of 3-chloro-5-methylbenzyl alcohol, m.p. 32°–34.5° C.

EXAMPLE 11

3-Chloro-5-methylbenzaldehyde

To a cold solution (−60° C.) of oxalyl chloride (14.88 ml) in 300 ml of CH$_2$Cl$_2$, dimethylsulfoxide (25.16 ml) in 75 ml of CH$_2$Cl$_2$ was added followed by the addition of 3-chloro-5-methylbenzyl alcohol (23 g) in 100 ml of CH$_2$Cl$_2$. To this cold mixture, triethylamine (103 ml) was slowly added (exothermic) over 20 minutes. The reaction mixture was then permitted to warm to room temperature over 1.5 hours. The mixture was then added to 1 L of water and the layers separated. The $CH_2Cl_2$ layer was repeatedly washed with water and then dried with $MgSO_4$. Concentration afforded 25.4 g of an oil which was chromatographed on silica gel. Elution with 60:40 hexane:$CH_2Cl_2$ gave 20.01 g of pure 3-chloro-5-methylbenzaldehyde.

EXAMPLE 12

3-Chloro-5-methylohenyl-(trichloromethyl)carbinol

A cold solution (-10° C.) of 3-chloro-5-methylbenzaldehyde (19.5 g) and chloroform (15.6 ml) in 76 ml of DMF was treated dropwise with a 5M methanolic KOH solution (17.16 ml). The reaction mixture was stirred for 2 hours at −10° C. and then poured into a cold mixture of 170 ml of 1N HCl and 170 ml of $CH_2Cl_2$ with vigorous stirring. The layers were separated and the aqueous phase further extracted with $CH_2Cl_2$ (2×200 ml). The combined organic layers were washed with water (3×100 ml) and then dried over $MgSO_4$. Concentration produced 38.17 g of a crude oil. Purification by silica gel chromatography with 50:50 hexane:$CH_2Cl_2$ as eluant gave 32.3 g of pure trichloromethyl carbinol.

EXAMPLE 13

3-Chloro-5-(trichlorovinyl)toluene

To a suspension of $PCl_3$ (13.75 g) in 275 ml of $CH_2Cl_2$, a solution of (3-chloro-5-methyl- phenyl)-(trichloromethyl)-carbinol (17.87 g) in 125 ml of $CH_2Cl_2$ was added dropwise. The reaction mixture was stirred for 30 minutes prior to the addition of an additional 8 g of $PCl_5$. The reaction mixture was stirred for a total of 3 hours at ambient temperature prior to aqueous workup which afforded 19.35 g of pentachloro product.

A solution of the pentachloro adduct (3.62 g) in 26 ml of methanol was added dropwise to a solution of NaOH (554 mg) in methanol (17 ml) over 15 minutes. The reaction mixture was stirred at room temperature for an additional 15 hours at which point HCl was added to adjust the pH of the mixture to about 3. The solution was concentrated and then partitioned between water and ether. Repeated extractions with ether afforded 3.36 g of oil upon evaporation. This material was chromatographed on silica gel (hexane as eluant) to give 2.93 g of 3-chloro-5-(trichlorovinyl)toluene.

EXAMPLE 14

3-Chloro-5-(trichlorovinyl)benzyl bromide

A solution of 3-chloro-5-(trichlorovinyl)toluene (7.56 g) and dibenzoyl peroxide (0.5 g) in 250 ml of benzene was heated at reflux. N-Bromosuccinimide (6.04 g) was added in portions and the reaction mixture stirred at reflux for 3 hours. The mixture was then evaporated and the residue titurated with hexane (200 ml). The precipitated succinimide was removed by filtration and washed with hexane (2 x 25 ml). The hexane was concentrated and the residual oil (10.1 g) chromatographed on silica with petroleum ether as eluant. The column afforded 1.39 g of starting toluene, 1.18 g of dibromide, and 6.57 g of the desired benzyl bromide.

EXAMPLE 15

3-Chloro-5-(trichlorovinyl)benzyl azide

A solution of 3-chloro-5-(trichlorovinyl)benzyl bromide (3.57 g) and sodium azide (813 mg) in 50 ml of ethanol was heated at reflux for 30 minutes. The reaction was then concentrated and the residue chromatographed on silica gel with petroleum ether as eluant to afford 2.24 g of pure 3-chloro-5-(trichlorovinyl)benzyl azide.

EXAMPLE 16

5-Amino-1-[3-chloro-5-(trichlorovinyl)benzyl]-1,2,3triazole-4-carboxamide

Method A

A solution of cyanoacetamide (412 mg) in dimethyl formamide (DMF) (10 ml) and hexane (2 ml) was treated with NaH (50% dispersion, 470 mg) at ambient temperatures for 25 minutes. The solution was then filtered through celite and rinsed with DMF (2×2 ml). The filtrate was then cooled to 0° C. To this cold solution a solution of 3-chloro-5-(trichlorovinyl)benzyl azide (980 mg) in 18 ml of DMF was added dropwise over 10 minutes. The resulting mixture was stirred for 45 minutes at 0° C. and then poured into 50 ml of water containing 5 ml of glacial acetic acid. The precipitate was collected and washed repeatedly with water and with hexane. The solid was recrystallized from ethanol (11 ml) to give 345 mg of pure product, m.p. 191°–193.5° C.

Method B

A solution of 5-amino-1,2,3-triazole-4-carboxamide (386 mg) in 12 ml of dry dimethylformamide (DMF) was treated with sodium hydride (50% dispersion in mineral oil, 154 mg). The reaction mixture was stirred at ambient temperature for 20 minutes at which point a solution of 3-chloro-5-(trichlorovinyl)benzyl bromide (1.01 g) in 6 ml of DMF was added dropwise. The resulting mixture was stirred for 1 hour at room temperature and then poured into 50 ml of water. Acetic acid was added to adjust the pH to 6.0. The aqueous mixture was then extracted with methylene chloride (2×75 ml). The organic layers were back-washed with water, dried with anhydrous magnesium sulfate and then concentrated under vacuum. The residue was chromatographed on silica gel (97:3 methylene chloride: methanol) to give: 4-amino-1-[3-chloro-5-(trichlorovinyl)benzyl]-1,2,3-triazole-5-carboxamide (497 mg) and 5-amino-1-[3-chloro-5-(trichlorovinyl)benzyl]1,2,3-triazole-4-carboxamide (346 mg).

EXAMPLE 17

4-Chloro-3-(trichlorovinyl)toluene

A cold (−10° C.) solution of 2-chloro-5-methylbenzaldehyde (20.8 g) and chloroform (16.6 ml) in 81 ml of dimethylformamide (DMF) is treated dropwise with a methanolic KOH solution (6.08 g in 18.3 ml). The reaction mixture is stirred for 2 hours at −10° C. and then poured into a mixture of 1N HCl (185 ml) and 185 ml of $CH_2Cl_2$. The layers are separated and the aqueous layer further extracted with $CH_2Cl_2$ (2×75 ml). The combined organic layers were washed with water (3x), dried with anhydrous magnesium sulfate and concentrated under reduced pressure. The residue (40 g) was chromatographed on silica with 1:1 hexane/$CH_2Cl_2$ to give 24.49 g of trichloromethyl carbinol.

To a suspension of $PCl_5$ (12.4 g) in 250 ml of $CH_2Cl_2$, a solution of the trichloromethyl carbinol (24.49 g) in 100 ml of $CH_2Cl_2$ was added dropwise. The reaction mixture was stirred for 15 minutes at which point an additional 7.5 g of $PCl_3$ was added. The reaction mixture was stirred for an additional hour at room temperature and then carefully poured into 500 ml of ice-water. The layers were separated and the organic layer was washed with water, saturated NaHCO$_3$ solution, and water again. Evaporation afforded 25 g of an oil which was chromatographed on silica (petroleum ether) to give 18.6 g of the pentachloride adduct.

This pentachloride adduct (17.6 g) was added to a solution of 3.1 g of NaOH in 150 ml of methanol and the resulting mixture stirred for 16.5 hours at room temperature. The reaction mixture was neutralized with HCl (pH 6) and then concentrated under reduced pressure. The residue was partitioned between ether (400 ml) and water (100 ml). The layers were separated and the organic layer further washed with water and then dried with anhydrous magnesium sulfate. Concentration gave an oil which was distilled at 93°–95°/3 mm to give pure 4-chloro-3-(trichlorovinyl)toluene, 14.0 g.

EXAMPLE 18

4-Chloro-3-(trichlorovinyl)benzyl bromide

A solution of 4-chloro-3-(trichlorovinyl)toluene (13.77 g) and dibenzoyl peroxide (1.0 g) in 500 ml of benzene was heated at reflux. N-Bromosuccinimide (11.6 g) was added in portions and the resulting mixture stirred at reflux for 1.5 hours (negative KI test). The reaction mixture was concentrated under reduced pressure. The residue was partially dissolved in 300 ml of petroleum ether and the insoluble succinimide removed by filtration. The filtrate was concentrated to give 17.9 g of the benzyl bromide.

EXAMPLE 19

5-Amino-1-[4-chloro-3-(trichlorovinyl)benzyl]-1,2,3-triazole-4-carboxamide

A solution of 5-amino-1,2,3-triazole-4-carboxamide (1.65 g) in 50 ml of dry dimethylformamide (DMF) was treated with sodium hydride (50% in mineral oil, 658 mg) and heated to 40° C. for 20 minutes. To this mixture a solution of 4-chloro-3-(trichlorovinyl)benzyl bromide (4.4 g) in 10 ml of DMF was added and heating was continued at 40° C. for 1 hour. The reaction mixture was slowly added to 250 ml of water and the pH of the resulting solution adjusted with acetic acid to neutrality. The aqueous mixture was extracted with methylene chloride. The organic layers were then back-washed with water (4X's), dried with magnesium sulfate and concentrated. The residue was chromatographed on silica gel (97:3 CH$_2$Cl$_2$:CH$_3$OH) to give: 4-amino-1-[4-chloro-3-(trichlorovinyl)benzyl]-1,2,3-triazole-5-carboxamide (963 mg) and 5-amino-1-[4-chloro-3-(trichlorovinyl)benzyl]-1,2,3-triazole-4-carboxamide (650 mg), m.p. 174°–175° C.

EXAMPLE 20

3-Methyl-5-nitrobenzyl alcohol

A solution of 5-nitro-m-xylene (100 g) and dibenzyl peroxide (5.0 g) in 1.35 L of benzene was heated at reflux. In portions N-bromosuccinimide (128 g) is added over 15 minutes. The reaction mixture is heated for an additional hour at which point the mixture gave a negative KI test. The reaction mixture was evaporated and the residue treated with 1 L of hexane. The precipitated succinimide was removed by filtration. The filtrate was concentrated to give 174 g of a yellowish oil.

The crude benzylic bromide was dissolved in acetic acid (450 ml) to which was added 100 g of potassium acetate. The resulting solution was heated at reflux for 1 hour and then concentrated. The residue was partitioned between water (1 L) and ether (2×500 ml). The layers were separated and the combined organic layers were washed with saturated NaHCO$_3$ and brine. Concentration afforded 142.7 g of crude benzylic acetate.

The crude benzylic acetate product was dissolved in 250 ml of methanol and treated with 75 ml of a 5N methanolic KOH solution. After 30 minutes the reaction mixture was neutralized with acetic acid and concentrated. The residue was partitioned between water (500 ml) and ether (500 ml). The ethereal layer was washed with brine, dried with magnesium sulfate, and concentrated to give 131.5 g. The crude product was chromatographed on silica gel with methylene chloride to give 60.69 g of 3-methyl-5-nitrobenzyl alcohol, m.p. 56.8°–57.9° C.

EXAMPLE 21

3-Methyl-5-nitrobenzaldehyde

To a cold (−60° C.) solution of oxalyl chloride (7.08 ml) in 177 ml of CH$_2$Cl$_2$, dimethylsulfoxide (12 ml) in 35 ml of CH$_2$Cl$_2$ added slowly followed by the addition of 3-methyl-5-nitro benzaldehyde (11.84 g) in 50 ml of CH$_2$Cl$_2$. To this cold mixture, triethylamine (50 ml) was slowly added. The reaction mixture was then permitted to come to room temperature over the next hour. The reaction mixture was poured into 500 ml of water and the layers separated. The organic layer was repeatedly washed with water and dried over anhydrous magnesium sulfate. Concentration afforded an oil (12.1 g) which was used in the next reaction without further purification.

EXAMPLE 22

3-(Trichlorovinyl)-5-nitrotoluene

A cold solution (−10° C.) of 3-methyl-5-nitrobenzaldehyde (60.6 g) and chloroform (45.4 ml) in 220 ml of dimethylformamide (DMF) was treated dropwise with a 5N methanolic solution of KOH (49.73 ml). The reaction mixture was stirred at −10° C. for 2 hours and then poured into a cold mixture of CH$_2$Cl$_2$ (500 ml) and 1N HCl (500 ml) with vigorous stirring. The layers were then separated. The aqueous layer was further extracted with CH$_2$Cl$_2$ (1×500 ml). The combined organic layers were repeatedly washed with water, dried over magnesium sulfate and concentrated under reduced pressure. The residue was chromatographed on silica gel (80:20 CH$_2$Cl$_2$:hexane) to give 73 g of the trichloromethyl carbinol derivative.

To a suspension of PCl$_5$ (28.8 g) in 700 ml of CH$_2$Cl$_2$, a solution of 59.47 g of the trichloromethyl carbinol derivative in 300 ml of CH$_2$Cl$_2$ was added dropwise. After stirring the reaction mixture for 15 minutes, an additional 14.5 g of PCl$_5$ was added and the reaction mxture stirred overnight. The mixture was then poured slowly into 2 L of ice/water and the layers separated. The organic layer was washed with saturated NaHCO$_3$, water and then dried over magnesium sulfate. Concentration gave 61.52 g of the tetrachloro derivative.

A solution of 61.0 g of this tetrachloro derivative in 420 ml of methanol was added dropwise to a solution of NaOH (10.96 g) in 463 ml of methanol. The reaction mixture was stirred overnight at room temperature. The pH of the mixture was then adjusted to near 6 with glacial acetic acid. The reaction mixture was concentrated and the resulting residue partitioned between ether (800 ml) and water (500 ml). The layers were separated and the aqueous layer further extracted with 500 ml of ether. The combined organic layers were washed with water (3×300 ml) and then dried over magnesium sulfate. Concentration afforded 53.23 g of 3-(trichlorovinyl)-5-nitrotoluene.

EXAMPLE 23

3-Methyl-5-(trichlorovinyl)Aniline

To a warm solution of 3-(trichlorovinyl)-5-nitrotoluene (10.95 g) in 150 ml of ethanol, an aqueous solution of ammonium sulfide (30 ml of a commercial 46–52% aqueous solution diluted to 90 ml with water) was added in one portion. The resulting heterogeneous solution was heated in a 100° C. oil bath for 30 minutes. The hot reaction mixture was filtered and the precipitate thoroughly washed with ethanol. The filtrate was diluted with 1.2 L of brine and then extracted with methylene chloride (2×400 ml). The combined organic layers were washed with brine and dried over anhydrous magnesium sulfate. Concentration afforded 9.36 g of an oil.

EXAMPLE 24

3-Methyl-5-(trichlorovinyl)benzenediazonium hexafluorophosohate

3-Methyl-5-(trichlorovinyl)aniline (9.9 g) was mixed with 32 ml of concentrated HCl and 75 ml of water. The resulting suspension was cooled to −10° C. and a solution of sodium nitrite (3.5 g in 7 ml $H_2O$) was added dropwise. The reaction mixture was stirred at −10° C. for 10 minutes and then at 0° C. for 30 minutes. The cold (−10° C.) solution was filtered and the filtrate treated with 10 ml of a 60% solution of $HPF_6$. The mixture was shaken (0° C.) for 20 minutes and then filtered. The collected salt was washed with cold water repeatedly and dried in a vacuum oven at room temperature over $P_2O_5$ to give 11.30 g of the desired hexafluorophosphate salt.

EXAMPLE 25

3-Bromo-5-(trichlorovinyl)toluene

To a suspension of $CuBr_2$ (14.1 g) in dimethylsulfoxide (DMSO), a solution of 3-methyl-5-(trichlorovinyl)-benzenediazonium hexafluorophosphate (11.3 g) in 35 ml of DMSO was added. The reaction mixture was stirred at 25° C. for 15 minutes and then at 35° C. for 10 minutes. The reaction mixture was cooled (0° C.) and then diluted with 500 ml of ice water. The aqueous solution was extracted with ether (3×150 ml). The combined ethereal layers were washed with brine (2×100 ml), dried with magnesium sulfate and concentrated to give 7.77 g of an oil. Chromatography on silica gel (Hexane) afforded 6.88 g of pure product.

EXAMPLE 26

3-Bromo-5-(trichlorovinyl)benzyl bromide

A solution of 3-bromo-5-(trichlorovinyl)toluene (1.76 g) and 100 mg of dibenzoyl peroxide in 100 ml of benzene was heated at reflux. N-bromosuccinimide (1.3 g) was added in portions and the reaction mixture stirred at reflux for 5.5 hours. The reaction mixture was concentrated and the residue triturated with 100 ml of hexane. The precipitated succinimide was collected by filtration and thoroughly washed with hexane. The filtrate was concentrated under reduced pressure to give 2.2 g of a crude mixture containing the desired benzyl bromide.

EXAMPLE 27

3-Bromo-5-(trichlorovinyl)benzyl azide

A solution of crude 3-bromo-5-(trichlorovinyl)benzyl bromide (2.2 g) and sodium azide (760 mg) in 30 ml of ethanol was heated at reflux for 1 hour. The reaction solution was concentrated under reduced pressure and the residue triturated with 100 ml of hexane. The mixture was filtered and the filtrate chromatographed on silica (hexane) to give 1.1 g of pure azide.

EXAMPLE 28

5-Amino-1-[3-bromo-5-(trichlorovinyl)benzyl]-1,2,3,-triazole-4-carboxamide

To a hot (60° C.) solution of cyanoacetamide (546 mg) in 20 ml of ethanol, 6.47 ml of a methanolic solution of NaOH (1N) was added and the resulting mixture was stirred at 60° C. for 20 minutes. A solution of 3-bromo-5-(trichlorovinyl)benzyl azide (1.02 g) in 10 ml of ethanol was added and the reaction mixture heated at 60° C. for two hours. The pH of the solution was adjusted to ~6 with acetic acid and then concentrated to a small volume. Dilution with 50 ml of water afforded a precipitate which was washed thoroughly with water. The precipitate was recrystallized from 8 ml of ethanol to give 466 mg of pure product, m.p. 175°–177° C.

EXAMPLE 29

2-(Trichlorovinyl)-p-xylene

A cold (−10° C.) solution of 2,5-dimethylbenzaldehyde (44.25 g) and chloroform (150.2 g) in 531 ml of dimethylformamide (DMF) was treated dropwise with a methanolic KOH solution (39.7 g of KOH in 119 ml of methanol). The reaction mixture was stirred for 2 hours at −8° C. at which point the reaction mixture was poured onto a cold mixture of 450 ml of benzene and 450 ml of a 1N HCl solution, the reaction mixture permitted to come to room temperature. The layers were then separated and the organic layer was further washed with water. Concentration under reduced pressure afforded 90.98 g of crude trichlorovinyl carbinol.

To a suspension of $PCl_3$ (75 g) in 1.5 L of $CH_2Cl_2$, a solution of the crude trichlorovinyl carbinol (90.98 g) in 400 ml of $CH_2Cl_2$ was added dropwise. The reaction mixture was stirred for 30 minutes at which point additional $PCl_5$ (45 g) was added. The reaction mixture was stirred for 3 hours and then subjected to aqueous workup which afforded 88.8 g of crude tetrachloro derivative.

A solution of this tetrachloro adduct (83.8 g) in 375 ml of methanol was added dropwise to a solution of NaOH (14.8 g) in methanol (750 ml). The resulting solution was stirred at ambient temperature for 29 hours. The reaction mixture was concentrated and then partitioned between ether and water. The ethereal fraction was dried with anhydrous magnesium sulfate, evaporated and chromatographed on silica gel. Elution with hexane gave 41.5 g of pure 2-(trichlorovinyl)-p-xylene.

EXAMPLE 30

4-Methyl-3-(trichlorovinyl)benzyl bromide

To a hot solution of 2-(trichlorovinyl)-p-xylene (25.4 g) and dibenzoyl peroxide (3.2 g) in 1000 ml of benzene, N-bromosuccinimide (20.79 g) was added in portions. The resulting mixture was heated at reflux for 15 minutes at which point no N-bromosuccinimide was evident. The reaction solution was evaporated and the residual oil suspended in 90:10 petroleum ether:methylene chloride (250 ml). The precipitated succinimide was collected by filtration and thoroughly washed with the above solvent system. The filtrate was concentrated and then chromatographed on silica gel. Elution with 90:10 petroleum ether:methylene chloride gave 20.9 g of a mixture containing 4-methyl-3-(trichlorovinyl)benzyl bromide and 4-methyl-2-(trichlorovinyl) benzyl bromide.

EXAMPLE 31

4-Methyl-3-(trichlorovinyl)benzyl alcohol

A solution of the crude mixture of benzyl bromides [4-methyl-3-(trichlorovinyl)benzyl bromide and 4-methyl-2-(trichlorovinyl)benzyl bromide, 29.32 g]in 700 ml of dry tetrahydrofuran was treated with 33.92 g of tetra-n-butyl ammonium acetate and stirred at room temperature for 1 hour. The reaction mixture was concentrated under reduced pressure and the residual oil triturated with 400 ml of hexane. The precipitate was removed by filtration and thoroughly washed with hexane (2×200 ml). Concentration gave 28.2 g of a yellow oil which was dissolved in 266 ml of methanol and treated dropwise with an aqueous 1N KOH solution (55 ml). The reaction mixture was stirred at ambient temperature for 30 minutes and then partially concentrated. The concentrate was then extracted with ether (1000 ml). The ethereal layer was back-washed with brine (2×200 ml), dried with anhydrous magnesium sulfate, and concentrated in vacuum to give 28.2 g of an oil. Chromatography on silica (90:10 methylene chloride:ether) gave 8.92 g of 4-methyl-2-(trichlorovinyl)benzyl alcohol and 10.67 g of the desired 4-methyl-3-(trichlorovinyl)benzyl alcohol.

EXAMPLE 32

4-Methyl-3-(trichlorovinyl)benzyl chloride

A solution of 4-methyl-3-(trichlorovinyl)benzyl alcohol (2.06 g) and triphenylphosphine (2.58 g) in 100 ml of carbon tetrachloride was heated at reflux for 48 hours. The reaction mixture was concentrated under reduced pressure and the residue dissolved in $CH_2Cl_2$ (200 ml). This organic solution was shaken with 30% $H_2O_2$ (10 ml) and then diluted with water (100 ml) and the layers separated. The organic layer was further washed with water, dried with anhydrous magnesium sulfate and concentrated to give 4.37 g of crude product. Chromatography on silica (1:1 hexane:methylene chloride) gave 1.81 g of 4-methyl-(trichlorovinyl)benzyl chloride.

EXAMPLE 33

4-Methyl-3-(trichlorovinyl)benzyl azide

A solution of 4-methyl-3-(trichlorovinyl)benzyl chloride (1.81 g ) and sodium azide (650 mg) in 20 ml of ethanol was heated at reflux for 5 hours. The reaction mixture was concentrated and then chromatographed on silica gel. Elution with 1:1 hexane:methylene chloride afforded 1.65 g of pure azide.

EXAMPLE 34

5-Amino-1-[4-methyl-3-(trichlorovinyl)benzyl]-1,2,3-triazole-4-carboxamide

To a hot (60° C.) solution of cyanoacetamide (1.09 g) in 30 ml of ethanol, 13 ml of a methanolic solution of NaOH (1N) was added and the resulting mixture was stirred at 60° C. for 20 minutes. At this point a solution of 4-methyl-3-(trichlorovinyl)benzyl azide (1.65 g) in 10 ml of ethanol was added and the reaction mixture stirred at 60° C. for an additional two hours. The precipitate was removed by filtration and rinsed with ethanol and ether. The filtrate was diluted with water (200 ml) and the resulting precipitate collected (1.56 g). The crude product was chromatographed on silica with 95:5 methylene chloride:methanol to give 889 mg of 5-amino-1-[4-methyl-3-(trichlorovinyl)benzyl]-1,2,3- triazole-4-carboxamide, m.p. 196°–197° C.

EXAMPLE 35

3-Methyl-5-(trichlorovinyl)benzyl bromide

To a refluxing solution of 5-(trichlorovinyl)-m-xylene (32.28 g) and dibenzoyl peroxide (3.43 g) in 1300 ml of benzene, N-bromosuccinimide (30.21 g) was added in portions. The resulting mixture was heated at reflux for 30 minutes at which point no N-bromosuccinimide was evident. The reaction mixture was concentrated under reduced pressure and the residue triturated with 250 ml of hexane. The precipitated succinimide was collected by filtration and thoroughly washed with hexane. The filtrate was concentrated and the residue chromatographed on silica (petroleum ether) to give 26.2 g of the desired benzyl bromide.

EXAMPLE 36

3-Methyl-5-(trichlorovinyl)benzyl azide

A solution of 3-methyl-5-(trichlorovinyl)benzyl bromide (3.14 g) and sodium azide (1.0 g) in 25 ml of ethanol was heated at reflux for 2 hours. The reaction mixture was concentrated under reduced pressure and the resulting oil triturated with 50 ml of hexane. The mixture was filtered and the filtrate concentrated to give 2.64 g of azide.

EXAMPLE 37

5-Amino-1-[3-methyl-5-(trichlorovinyl)benzyl]-1,2,3-triazole-4-carboxamide

To a hot (60° C.) solution of cyanoacetamide (1.8 g) in 57 ml of ethanol, 21.3 ml of a 1N methanolic solution of NaOH was added and the resulting mixture stirred for 20 minutes. A solution of 3-methyl-5-(trichlorovinyl)benzyl azide (2.64 g) in 20 ml of ethanol was added and the reaction mixture stirred at 60° C. for an additional two hours. The pH of the solution was adjusted to 6 with acetic acid. The solution was diluted with water (300 ml) and the resulting preipitate collected and rinsed thoroughly with water. The solid was then chromatographed on silica gel (97:3) $CH_2Cl_2$:$CH_3OH$) to give 980 mg of pure triazole.

EXAMPLE 38

3-Methyl-5-(trichlorovinyl)benzyl alcohol

A suspension of potassium acetate (4.4 g) and 3-methyl-5-(trichlorovinyl)benzyl bromide (7.2 g) in 50 ml of glacial acetic acid was heated at reflux for two hours. The reaction mixture was concentrated and the residue partitioned between ether (150 ml) and water (150 ml). The layers were separated and the aqueous phase further extracted with ether. The combined ethereal layers were washed with saturated NaHCO$_3$ and water and then dried with anhydrous magnesium sulfate. Concentration afforded the crude acetate which was dissolved in 50 ml of methanol and treated with 4.5 g of KOH. The resulting mixture was stirred at room temperature for 45 minutes. The pH of the solution was adjusted to @6 with acetic acid. The reaction mixture was then concentrated and the residue partitioned between ether (150 ml) and water (150 ml). The layers were separated and the ethereal layer concentrated to give 6.5 g of an oil which was chromatographed on silica gel (80:10:10 hexane:methylene chloride:ethyl acetate) to give 5.8 g of pure alcohol, m.p. 63°–65.5° C.

EXAMPLE 39

3-Methyl-5-(trichlorovinyl)benzaldehyde

To a cold (−60° C.) solution of oxalyl chloride (3.17 ml) in 65 ml of dry methylene chloride (CH$_2$Cl$_2$), dimethyl sulfoxide (DMSO) (5.37 ml) in 16 ml of CH$_2$Cl$_2$ was added followed by the addition of 7.86 g of 3-methyl-5-(trichlorovinyl)benzyl alcohol in 16 ml of CH$_2$Cl$_2$, to this cold mixture, triethylamine (22 ml) was slowly added. The reaction mixture was permitted to warm to room temperature over 1.5 hours. The reaction mixture was then added to 200 ml of water and the layers separated. The organic layer was repeatedly washed with water and then dried with magnesium sulfate. Concentration afforded 8.16 g of an oil which was chromatographed on silica gel (60:40 hexane:CH$_2$Cl$_2$ to give 7.82 g of pure aldehyde, m.p. 42°–43° C.

EXAMPLE 40

3.5-Di(trichlorovinyl)toluene

A cold solution (−10° C.) of 3-methyl-5-(trichlorovinyl)benzaldehyde (7.72 g) and chloroform (3.8 ml) in 18.5 ml of dimethylformamide (DMF) was treated dropwise with a 5N methanolic solution of KOH (4.19 ml). The mixture was stirred at −10° C. for 2 hours and then poured into a cold mixture of 42 ml of 1N HCl and 42 ml of CH$_2$Cl$_2$ with vigorous stirring. The layers were separated and the aqueous layer further extracted with CH$_2$Cl$_2$. The combined organic layers were washed with water and then dried with MgSO$_4$. Concentration afforded 15.9 g of a yellow oil which was chromatographed on silica gel (70:30 CH$_2$Cl$_2$:hexane) to give 10.7 g of pure trichloromethyl carbinol.

A solution of this trichloromethyl carbinol (10.7 g) in 50 ml of CH$_2$Cl$_2$ was added dropwise to a suspension of PCl$_5$ (4.0 g) in 65 ml of CH$_2$Cl$_2$. The reaction mixture was stirred for 30 minutes at which point an additional 2.4 g of PCl$_5$ was added. The mixture was stirred at room temperature for 2 hours and then poured carefully into 250 ml of ice-water. The layers were separated and the aqueous layer further extracted with CH$_2$Cl$_2$. The combined organic layers were washed with water, saturated NaHCO$_3$ and brine. The organic solution was dried with MgSO$_4$ and concentrated to give 11.0 g of product. This material was dissolved 30 ml of methanol and treated with a solution of NaOH (1.7 g) in 70 ml of methanol. The reaction mixture was stirred at room temperature for 16 hours and then the pH adjusted to 6 with acetc acid. The mixture was concentrated under reduced pressure and the residue partitioned between ether (200 ml) and water (200 ml). The layers were separated and the aqueous phase further extracted with ether. The combined ethereal layers were washed with water and then dried with MgSO$_4$. Concentration afforded 9.63 g of 3,5-di(trichlorovinyl)toluene, m.p. 41.4°–44.6° C.

EXAMPLE 41

3.5-Di(trichlorovinyl)benzyl bromide

A solution of 3,5-di(trichlorovinyl)toluene (6.0 g) and dibenzoyl peroxide (200 mg) in 150 ml of benzene was heated at reflux. N-Bromosuccinimide (3.6 g) was added in portions and the reaction mixture stirred at reflux for 3 hours. The mixture was evaporated and the residue triturated with 200 ml of hexane. The precipitated succinimide was collected and the filtrate concentrated to five 7.9 g of crude benzyl bromide.

EXAMPLE 42

3,5-Di(trichlorovinyl)benzyl azide

A solution of crude 3,5-di(trichlorovinyl)benzyl bromide (7.9 g) and sodium azide (1.9 g) in 200 ml of ethanol was heated at reflux for 1.5 hours. The reaction mixture was concentrated and the residue partitioned between 100 ml of ether and 100 ml of water. The layers were separated and the aqueous phase further extracted with ether. The ethereal layers were washed with water, dried with MgSO$_4$, and concentrated to give 7.03 g of an oil. This material was chromatographed on silica gel (hexane then 90:10 hexane:CH$_2$Cl$_2$) to give 3.52 g of pure azide.

EXAMPLE 43

5-Amino-1-[3,5-di(trichlorovinyl)benzyl]-1,2,3-triazole-4-carboxamide

To a hot (60° C.) solution of cyanoacetamide (0.692 g) in 25 ml of ethanol, 8.2 ml of a 1N methanolic solution of NaOH was added and the resulting mixture stirred for 20 minutes. 3,5-Di(trichlorovinyl)benzyl azide (1.5 g) was added in one portion and the resulting mixture stirred at 60° C. for 1 hour. The pH of the mixture was adjusted to 6 with acetic acid. The reaction mixture was then concentrated to a reduced volume and diluted with 100 ml of water. The aqueous mixture was extracted with CH$_2$Cl$_2$ (3×100 ml). The combined organic layers were washed with water, dried with MgSO$_4$ and concentrated to give 1.5 g of crude product. This material was chromatographed on silica gel (95:5 CH$_2$Cl$_2$:CH$_3$OH) to give 890 mg of a solid. Recrystallization from 5 ml of ethanol provided pure triazole, m.p. 167°–169° C.

EXAMPLE 44

3-Fluoro-5-(trichlorovinyl)toluene

A mechanically stirred mixture of 3-methyl-5-(trichlorovinyl)benzenediazonium hexafluorophosphate (10 g) and sea sand (90 g) are immersed in an oil bath at 160°–165° C. The mixture is stirred for 10 minutes at this elevated temperature and then permitted to cool. The reaction mixture is triturated in 300 ml of ether and filtered. The filtrate is washed with aqueous sodium bicarbonate and water. The ether solution is dried with MgSO$_4$ and concentrated under reduced pressure. The residue is chromatographed on silica gel (hexane) to yield 3-fluoro-5-(trichlorovinyl))toluene.

EXAMPLE 45

3-Fluoro-5-(trichlorovinyl)benzyl bromide

To a solution of 3-fluoro-5-(trichlorovinyl)toluene (2.39 g) and dibenzoyl peroxide (0.2 g) in 60 ml of benzene at reflux, N-bromosuccinimide (2.21 g) is added in portions. The mixture is heated at reflux until the solution gives a negative reaction with potassium iodide. The reaction mixture is concentrated and the residue triturated with 100 ml of hexane. The precipitated succinimide is collected by filtration and the filtrate concentrated and then chromatographed on silica gel (hexane) to give the desired benzyl bromide.

EXAMPLE 46

3-Fluoro-5-(trichlorovinyl)benzyl azide

A solution of 3-fluoro-5-(trichlorovinyl)benzyl bromide (3.18 g) and sodium azide (0.975 g) in 25 ml of ethanol is heated at reflux for 2 hours. The reaction mixture is concentrated and the residue triturated with 50 ml of hexane. The mixture is filtered and the filtrate concentrated to give the desired azide.

EXAMPLE 47

5-Amino-1-[3-fluro-5-(trichlorovinyl)benzyl-1,2,3-triazole4-carboxamide

To a hot (60° C.) solution of cyanoacetamide (3.0 g) in 120 ml of ethanol, 42.6 ml of a 1N methanolic solution of NaOH is added. The resulting mixture is stirred for 20 minutes. A solution of 3-fluoro-5-(trichlorovinyl)-benzyl azide (5.2 g) in 40 ml of ethanol is added and the reaction mixture stirred at 60° C. for an additional hour. The mixture is cooled and then treated with acetic acid to adjust the pH to 6. The solution is then concentrated under vacuum to a small volume and diluted with water. The precipitate is collected by filtration and thoroughly washed with water. The solid is then chromatographed on silica gel (97:3 $CH_2Cl_2:CH_3OH$) to yield pure triazole.

EXAMPLE 48

3-Chloro-4-(trichlorovinyl)toluene

A cold (−10° C.) solution of 2-chloro-4-methylbenzaldehyde (15.96 g) and chloroform (18.6 g) in 62 ml of dimethylformamide (DMF) was treated dropwise with a methanolic solution of KOH (4.66 g in 14 ml). The reaction mixture was stirred at −10° C. for two hours and then poured into a cold mixture of 1N HCl (140 ml) and $CH_2Cl_2$ (140 ml) with vigorous stirring. The layers were separated and the aqueous layer further extracted with $CH_2Cl_2$. The combined organic layers were washed with water, dried with $MgSO_4$, and concentrated to give 15.1 g. Chromatography on silica gel (60:40 $CH_2Cl_2$:hexane) gave 12.88 g of trichloromethyl carbinol product.

To a suspension of $PCl_5$ (6.52 g) in 150 ml of $CH_2Cl_2$, a solution of the trichloromethyl carbinol (12.88 g) in 75 ml of $CH_2Cl_2$ was added dropwise. The reaction mixture was stirred for 30 minutes and then an additional 4.0 g of $PCl_5$ was added. The reaction mixture was stirred for 3 hours and then carefully subjected to aqueous work-up to give 13.11 g of crude product. Chromatography on silica gel (petroleum ether) provided 11.7 g of pure pentachloro derivative.

A solution of this pentachloro derivative (11.68 g) in 50 ml of methanol was added dropwise to a solution of NaOH (2.06 g) in methanol (100 ml). The reaction mixture was stirred at room temperature for 18 hours at which point the pH of the solution was adjusted to 6 with HCl. The reaction mixture was concentrated and then partitioned between ether (400 ml) and water (200 ml). The ethereal layer was dried with $MgSO_4$ and concentrated to give 10.1 g of 3-chloro-4-(trichlorovinyl)toluene.

EXAMPLE 49

3-Chloro-4-(trichlorovinyl)benzyl bromide

To a solution of 3-chloro-4-(trichlorovinyl) toluene (10.1 g) and dibenzoyl peroxide (726 mg) in 360 ml of benzene at reflux, N-bromosuccinimide (8.42 g) was added in portions. The mixture was heated at reflux for 2 hours at which point the mixture gave a negative KI response. The reaction mixture was concentrated and the residue triturated with 300 ml of petroleum ether. The mixture was filtered and the filtrate concentrated in vacuo to give 14.77 g of crude benzyl bromide.

EXAMPLE 50

5-Amino-1-[3-chloro-4-(trichlorovinyl)benzyl]-1,2,3-triazole-4-carboxamide

A solution of 5-amino-1,2,3-triazole-4-carboxamide (1.65 g) in 50 ml of dimethylformamide (DMF) was treated with NaH (50% in mineral oil, 658 mg) and stirred at room temperature for 20 minutes. To this mixture a solution of 3-chloro-4-(trichlorovinyl)benzyl bromide (5.7 g) in 10 ml of DMF was added and the resulting reaction mixture stirred for 1 hour. The mixture was carefully poured into 500 ml of water and the pH of the resulting solution adjusted to 6 with acetic acid. The mixture was then extracted with $CH_2Cl_2$ (2×400 ml). The organic layers were dried and concentrated. The resulting residue was chromatographed on silica gel (97:3 $CH_2Cl_2:CH_3OH$) to give: 4-amino-1-[3-chloro-4-(trichlorovinyl)benzyl]-1,2,3-triazole-5-carboxamide (2.28 g) and 5-amino-1-[3-chloro-4-(trichlorovinyl)benzyl]-1,2,3-triazole-4-carboxamide (1.2 g). This latter material was recrystallized from ethanol to give pure triazole, m.p. 185°–186.5° C.

EXAMPLE 51

3-(Trichlorovinyl)toluene

From the reaction of m-tolualdehyde (18.52 g) and chloroform (27.88 ml) in dimethylformamide (93 ml) with KOH (7.0 g) in methanol (21 ml) as in Example 29, 39.4 g of crude trichloromethyl carbinol was obtained. A suspension of $PCl_5$ (21.2 g) in 500 ml of $CH_2Cl_2$ was treated with the crude trichloromethyl carbinol as in Example 29. After 15 minutes at room temperature, an additional portion of $PCl_5$ (12.91 g) was added. Appropriate work-up yielded 39.2 g of crude tetrachloro derivative.

A solution of this tetrachloro derivative (39.2 g) in methanol was slowly added to a solution of NaOH (7.66 g) in methanol (370 ml) and stirred at room temperature for 24 hours. The reaction mixture was acidified to pH 6 with acetic acid and partially evaporated in vacuo. The oily residue was partitioned between ether (250 ml) and water (200 ml). The aqueous layer was further extracted with ether (200 ml). The combined extracts were washed with water and dried over $MgSO_4$. Concentration afforded the crude product which was purified by chromatography on silica gel (petroleum ether) to give 26.47 g of 3-(trichlorovinyl)toluene.

EXAMPLE 52

3-(Trichlorovinyl)benzyl azide

From the reaction of 3-(trichlorovinyl)toluene (4.35 g), dibenzoyl peroxide (0.363 g), and N-bromosuccinimide (4.21 g) in 180 ml of benzene as in Example 30, 6.56 g of crude benzyl bromide was obtained.

The reaction of this crude benzyl bromide (6.56 g) and sodium azide (1.92 g) in ethanol (90 ml) as in Example 33 gave 5.48 g of crude benzyl azide. Chromatography on silica gel yielded 3.29 g of pure 3-(trichlorovinyl)benzyl azide.

EXAMPLE 53

5-Amino-1-[3-(trichlorovinyl)benzyl]-1,2,3-triazole-4-carboxamide carboxamide From the reaction of cyanoacetamide (1.84 g), 3-(trichlorovinyl)benzyl azide (2.59 g) and 1N methanolic NaOH (22.2 ml) in ethanol (60 ml) as in Example 34, 2.03 g of crude triazole was obtained. After recrystallization from isopropanol, 1.35 g of pure 5-amino-1-[3-(trichlorovinyl)benzyl]-1,2,3-triazole-4-carboxamide, m.p. 186°–188° C., was obtained.

EXAMPLE 54

4-(Trichlorovinyl)toluene

From the reaction of p-tolualdehyde (18.52 g) and chloroform (27.88 g) in dimethylformamide (93 ml) with KOH (7.0 g) in methanol (21 ml) as in Example 29, 39.4 g of crude trichloromethyl carbinol was obtained.

A suspension of $PCl_5$ (21.2 g) in 500 ml of $CH_2Cl_2$ was treated with a solution of the crude carbinol (39.4 g) in 120 ml of $CH_2Cl_2$ as in Example 29. After 15 minutes at room temperature an additional portion of $PCl_5$ (12.91 g) was added. The same reaction conditions and work-up as in Example 29 yielded 41.7 g of crude tetrachloro derivative.

A solution of the tetrachloro adduct in methanol (100 ml) was slowly added to a solution of sodium hydroxide (7.66 g) in methanol (370 ml) and stirred at room temperature for 18 hours. The reaction mixture was acidified to pH 6 with acetic acid and partially evaporated in vacuo. The oily residue was partitioned between ether (250 ml) and water (200 ml). The aqueous layer was further extracted with an additional 200 ml of ether. The combined extracts were washed with water, dried with $MgSO_4$, and concentrated to yield the crude product. Purification on silica gel (petroleum ether) yielded 14.69 g of pure 4-(trichlorovinyl) toluene.

EXAMPLE 55

4-(Trichlorovinyl)benzyl azide

From the reaction of 4-(trichlorovinyl)toluene (4.35 g), dibenzoyl peroxide (0.363 g), and N-bromosuccinimide (4.21 g) in 180 ml of benzene at reflux as in Example 30, 6.7 g of crude benzyl bromide was obtained.

The reaction of this crude benzyl bromide (6.7 g) and sodium azide (1.92 g) in ethanol (90 ml) at reflux as in Example 33 yielded 5.7 g of crude benzyl azide. Chromatography on silica gel afforded 3.98 g of pure 4-(trichlorovinyl)benzyl azide.

EXAMPLE 56

5-Amino-1-[4-(trichlorovinyl)benzyl]-1,2,3-triazole-4-carboxamide

From the reaction of cyanoacetamide (1.84 g), 4-(trichlorovinyl)benzyl azide (2.59 g), and 1N NaOH (22.2 ml) in ethanol (60 ml) as in Example 34, 2.00 g of crude triazole was obtained. Recrystallization from isopropanol gave 0.867 g of pure 5-amino-1-[4-(trichlorovinyl)benzyl]-1,2,3-triazole-4-carboxamide, m.p. 200°–203° C.

EXAMPLE 57

3.5-Dichloro-4-(trichlorovinyl)toluene 2,6-Dichloro-4-methylaniline (30.4 g) was converted to 2,6-dichloro-4-methylbenzaldehyde (6.54 g) according to the general procedure of Jolad and Rajagopal (*Organic Synthesis, Collected Volume I*, pp 139–141). This aldehyde (2.44 g) was reacted with chloroform (2.40 g) and methanolic KOH (610 mg in 1.8 ml) in dimethylformamide (8 ml) according to the procedure described in Example 29 to give 3.5 g of crude trichloromethyl carbinol.

A suspension of $PCl_5$ (2.80 g) in 60 ml of $CH_2Cl_2$ was treated with a solution of the crude trichloromethyl carbinol (3.5 g) in 20 ml of $CH_2Cl_2$ as in Example 29. After 15 minutes at room temperature, an additional 1.6 g of $PCl_5$ was added. Appropriate reaction times and work-up as in Example 29 afforded 2.8 g of hexachloro product. A solution of this material (2.8 g) in 15 ml of methanol is added dropwise to a solution of NaOH (0.5 g) in 25 ml of methanol as in Example 29. The reaction mixture is stirred at room temperature for 15 hours at which point the pH of the solution is adjusted to 6 with hydrochloric acid. The reaction mixture is concentrated and partitioned between ether and water. The ethereal layer is dried and concentrated. The residue is chromatographed on silica gel to give pure 3,5-dichloro-4-(trichlorovinyl)toluene

EXAMPLE 58

3.5-Dichloro-4-(trichlorovinyl)benzyl azide

From the reaction of 3,5-dichloro-4-(trichlorovinyl)-toluene (2.15 g), dibenzoyl peroxide (0.33 g), and N-bromosuccinimide (2.05 g) in 85 ml of benzene at reflux as in Example 30, 3,5-dichloro-4-(trichlorovinyl)benzyl bromide is obtained. This material (2.7 g) and sodium azide (0.8 g) in ethanol (25 ml) is heated for 2 hours. The crude product is chromatographed on silica gel to give pure 3,5-dichloro-4-(trichlorovinyl)benzyl azide.

EXAMPLE 59

5-Amino-1-[3,5-dichloro-4-(trichlorovinyl)benzyl]1,2,3-triazole-4-carboxamide From the reaction of cyanoacetamide (0.92 g), 3,5-dichloro-4-(trichlorovinyl)benzyl azide (1.25 g), and 1N methanolic NaOH (11.1 ml) in ethanol (30 ml) as in Example 34, crude triazole is obtained. This material is chromatographed on silica gel to give pure 5-amino-1-[3,5-dichloro-4-(trichlorovinyl)benzyl]-1,2,3-triazole-4-carboxamide.

EXAMPLE 60

5-(Trifluoromethyl)-m-xylene

A solution of 5-iodo-m-xylene (2.3 g) in dimethylformamide (DMF)(30 ml) and copper bronze (0.65 g) in a stainless steel tube is cooled and treated with trifluoromethyliodide (15 g). The tube is sealed and heated at 130°-140° C. in a rocking autoclave for 6 hours. After cooling and venting, the reaction mixture is diluted with water and extracted with n-hexane (2×200 ml). The combined hexane extracts are washed with aqueous NaHCO₃ and water. After drying over MgSO₄, the solvent is removed under reduced pressure. The residue is subjected to chromatography over silica gel to yield purified 5-(trifluoromethyl)-m-xylene.

EXAMPLE 61

3-Trifluoromethyl-5-methylbenzyl bromide

A solution of 5-trifluoromethyl-m-xylene (3.4 g) and dibenzoyl peroxide (0.25 g) in 100 ml of benzene at reflux is treated with N-bromosuccinimide (4.4 g) in portions. The mixture is heated until a negative potassium iodide test is obtained. The reaction mixture is cooled and concentrated in vacuo. The residue is triturated with n-hexane and the solids are removed by filtration. The filtrate is evaporated to give the oily crude benzyl bromide.

EXAMPLE 62

3-Trifluoromethyl-5-methylbenzyl alcohol

The crude benzyl bromide (5.3 g) is dissolved in acetic acid (50 ml) and treated with potassium acetate (2.9 g). The mixture is heated at reflux for 2 hours. The solvent is removed and the residue extracted with ether. The ether extracts are washed with aqueous NaHCO₃ and water. After drying with MgSO₄, the ethereal solution is evaporated to yield the crude benzyl acetate which is then hydrolyzed to the benzyl alcohol with methanolic KOH as in Example 10. The crude product is then chromatographed on silica gel to give 3-trifluoromethyl-5-methylbenzyl alcohol.

EXAMPLE 63

3-Trifluoromethyl-5-methylbenzaldehyde

A solution fo oxalyl chloride (2.8 ml) in 20 ml of CH₂Cl₂ is treated with a solution of dimethyl sulfoxide (DMSO)(5.0 ml) in 15 ml of CH₂Cl₂ at −60° C. as in Example 11 To this mixture is added the 3-trifluoromethyl-5-methylbenzyl alcohol (5.4 g) in CH₂Cl₂ (20 ml) followed by 20 ml of triethlyamine. Appropriate reaction conditions and work-up as in Example 11 afforded 3-trifluoro- methyl-5-methylbenzaldehyde.

EXAMPLE 64

3-Trifluoromethyl-5-trichlorovinyltoluene

The reaction of 3-trifluoromethyl-5-methylbenzaldehyde (5.8 g) and chloroform (3.8 ml) in DMF (20 ml) with 5N methanolic KOH (4.19 ml) as in Example 29 yields the crude trichloromethyl carbinol. This material as a solution in CH₂Cl₂ (50 ml) is added to a stirred suspension of PCl₅ (4.0 g) in 65 ml of CH₂Cl₂ at room temperature. After 15 minutes an additional portion of PCl₅ (2.4 g) is added. The reaction condition and work-up is the same as in Example 29. This crude tetrachloro derivative is dissolved in 50 ml of methanol and treated with a solution of NaOH (2.2 g) in methanol (30 ml). The reaction mixture is stirred for 16 hours and then treated with acetic acid to adjust the pH of the mixture to 6. The reaction mixture is concentrated and the residue partitioned between ether and water. The layers are separated and the aqueous phase repeatedly extracted with ether. The combined organic layers are washed with brine, dried with MgSO₄, and concentrated under reduced pressure. The crude product is chromatographed on silica gel to yield pure 3-trifluoromethyl-5-trichlorovinyltoluene.

EXAMPLE 65

3-Trifluoromethyl-5-trichlorovinylbenzyl azide

A solution of 3-trifluoromethyl-5-trichlorovinyltoluene (2.89 g) and dibenzoyl peroxide (0.2 g) in benzene (40 ml) at reflux is treated with N-bromosuccinimide (2.21 g) as in Example 30. The hexane soluble portion affords the crude benzyl bromide (3.67 g) which when heated with sodium azide (0.975 g) in ethanol (30 ml) at reflux for 2 hours as in Example 33 provides the desired benzyl azide.

EXAMPLE 66

5-Amino-1-[3-(trifluoromethyl)-5-(trichlorovinyl)benzyl]-1,2,3-triazole-4-carboxamide From the reaction of 3-trifluoromethyl-5-trichlorovinylbenzyl azide (1.07 g) and cyanoacetamide (0.616 g) in 20 ml of ethanol with 1N methanolic NaOH (7.4 ml) as in Example 34, one obtains the crude triazole derivative. Chromatography on silica gel (97:3 CH₂Cl₂: CH₃OH) provides purified 5-amino-1-[3-(trifluoromethyl)-5-(trichlorovinyl)benzyl]-1,2,3-triazole-4-carboxamide.

What is claimed is:

1. A method for preventing or treating coccidiosis which comprises administering to an animal in need of such treatment, an effective amount of a compound having the formula:

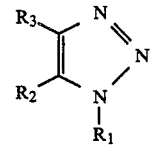

wherein:
R₁ is phenyl, phenyl loweralkyl, substituted phenyl or substituted phenyl loweralkyl wherein the substituents are 1 to 5 of halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

R₁ may also be phenacyl, naphthyl, or naphthylmethyl;

R₂ is amino, mono or diloweralkyl amino, acetamido, acetimido, ureido, formamido, formimido or guanidino; and R₃ is carbamoyl, cyano, carbazoyl, amidino or N-hydroxycarbamoyl.

2. The method of claim 1 wherein R₁ is mono-, di-, or tri-substituted phenyl or mono-, di-, or tri-substituted benzyl wherein the substituents are halogen, cyano, trifluoromethyl, trichlorovinyl or methyl;
R₂ is amino and
R₃ is carbamoyl.

3. The method of claim 2 wherein:
R₁ is di- or tri-substituted phenyl or di-or tri-substituted benzyl wherein the substituents are in the meta and/or para positions and are chloro, cyano, methyl, trifluoromethyl or trichlorovinyl.

4. A composition useful for the prevention and treatment of coccidiosis which comprises an inert carrier and a compound having the formula:

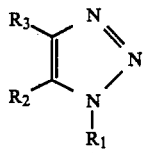

wherein:
$R_1$ is phenyl, phenyl loweralkyl, substituted phenyl or substituted phenyl loweralkyl wherein the substituents are 1 to 5 of halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

$R_1$ may also be phenacyl, naphthyl, or naphthylmethyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl.

5. The composition of claim 4 wherein $R_1$ is mono-, di-, or tri-substituted phenyl or mono-, di-, or tri-substituted benzyl wherein the substituents are halogen, cyano, trifluoromethyl, trichlorovinyl or methyl;

$R_2$ is amino and $R_3$ is carbamoyl.

6. The composition of claim 5 wherein:

$R_1$ is di- or tri-substituted phenyl or di- or tri-substituted benzyl wherein the substituents are in the meta and/or para positions and are chloro, cyano, methyl, trifluoromethyl or trichlorovinyl.

* * * * *